(12) United States Patent
Koh et al.

(10) Patent No.: US 7,171,271 B2
(45) Date of Patent: Jan. 30, 2007

(54) SYSTEM AND METHOD FOR EVALUATING HEART FAILURE USING AN IMPLANTABLE MEDICAL DEVICE BASED ON HEART RATE DURING PATIENT ACTIVITY

(75) Inventors: Steve Koh, South Pasadena, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 127 days.

(21) Appl. No.: 10/844,078

(22) Filed: May 11, 2004

(65) Prior Publication Data

US 2005/0256545 A1 Nov. 17, 2005

(51) Int. Cl.
*A61N 1/365* (2006.01)

(52) U.S. Cl. .................................................. 607/19

(58) Field of Classification Search ................ 600/510, 600/513, 519, 508; 607/17–19
See application file for complete search history.

(56) References Cited

U.S. PATENT DOCUMENTS

| | | | |
|---|---|---|---|
| 4,860,751 A | 8/1989 | Callaghan | 128/419 PG |
| 5,328,460 A | 7/1994 | Lord et al. | 604/67 |
| 5,514,162 A | 5/1996 | Bornzin et al. | 607/19 |
| 6,002,963 A | 12/1999 | Mouchawar et al. | 607/18 |
| 6,045,513 A | 4/2000 | Stone et al. | 600/508 |
| 6,190,324 B1 | 2/2001 | Kieval et al. | 600/483 |
| 6,249,705 B1 | 6/2001 | Snell | 607/59 |
| 6,280,409 B1 | 8/2001 | Stone et al. | 604/67 |
| 6,512,952 B2 | 1/2003 | Stahmann et al. | 607/9 |
| 6,572,557 B2 | 6/2003 | Tchou et al. | 600/483 |
| 6,628,988 B2 | 9/2003 | Kramer et al. | 607/9 |
| 6,643,546 B2 | 11/2003 | Mathis et al. | 607/9 |
| 6,741,885 B1 * | 5/2004 | Park et al. | 600/509 |
| 2001/0037067 A1 | 11/2001 | Tchou et al. | 600/483 |
| 2002/0115939 A1 | 8/2002 | Mulligan et al. | 600/510 |
| 2003/0055461 A1 * | 3/2003 | Girouard et al. | 607/17 |
| 2003/0149367 A1 | 8/2003 | Kroll et al. | 600/483 |
| 2003/0149453 A1 * | 8/2003 | Kroll et al. | 607/17 |
| 2004/0019365 A1 | 1/2004 | Ding et al. | 607/17 |
| 2005/0215914 A1 * | 9/2005 | Bornzin et al. | 600/508 |

FOREIGN PATENT DOCUMENTS

| | | |
|---|---|---|
| EP | 0920885 A1 | 6/1999 |
| WO | WO 00/64336 A1 | 11/2000 |

OTHER PUBLICATIONS

Kenneth A. Ellenbogen MD et al., *Clinical Cardiac Pacing* (W.B. Saunders)(1995), pp. 434-436.

* cited by examiner

*Primary Examiner*—George R. Evanisko

(57) ABSTRACT

Techniques are provided for detecting and tracking heart failure based on heart rate, rest rate and activity levels. Briefly, histograms are generated based on rest-rate adjusted heart rate values and corresponding activity level values. Heart failure is then detected and tracked based on an analysis of the histogram. In one example, so long as the activity level of the patient exceeds some minimum threshold, the ratio of adjusted heart rate to activity level is periodically calculated and resulting values are stored in a histogram. Each day, the histogram is compared against a previous histogram to detect any overall trend. For example, the centroid of the histogram can be calculated each day with any changes in the centroid values used to track progression of heart failure.

26 Claims, 9 Drawing Sheets

SYSTEM AND METHOD FOR EVALUATING HEART FAILURE USING AN IMPLANTABLE MEDICAL DEVICE BASED ON HEART RATE DURING PATIENT ACTIVITY

FIELD OF THE INVENTION

The invention generally relates to implantable medical devices, such as pacemakers or implantable cardioverter/defibrillators (ICDs), and in particular to techniques for detecting and tracking heart failure within a patient in which a medical device is implanted.

BACKGROUND

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation deprives vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive. As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. A particularly severe form of heart failure is congestive heart failure (CHF) wherein the weak pumping of the heart leads to build-up of fluids in the lungs and other organs and tissues.

Heart failure has been classified by the New York Heart Association (NYHA) into four classes of progressively worsening symptoms and diminished exercise capacity. Class I corresponds to no limitation wherein ordinary physical activity does not cause undue fatigue, shortness of breath, or palpitation. Class II corresponds to slight limitation of physical activity wherein such patients are comfortable at rest, but wherein ordinary physical activity results in fatigue, shortness of breath, palpitations or angina. Class III corresponds to a marked limitation of physical activity wherein, although patients are comfortable at rest, even less than ordinary activity will lead to symptoms. Class IV corresponds to inability to carry on any physical activity without discomfort, wherein symptoms of heart failure are present even at rest and increased discomfort is experienced with any physical activity.

The current standard treatment for heart failure is typically centered on drug treatment using angiotensin converting enzyme (ACE) inhibitors, diuretics or digitalis. Cardiac resynchronization therapy (CRT) may also be employed, if a bi-ventricular pacing device is implanted. Briefly, CRT seeks to normalize asynchronous cardiac electrical activation and resultant asynchronous contractions associated with heart failure by delivering synchronized pacing stimulus to both ventricles. The stimulus is synchronized so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis et al., entitled "Multi-Electrode Apparatus And Method For Treatment Of Congestive Heart Failure"; U.S. Pat. No. 6,628,988 to Kramer et al., entitled "Apparatus And Method for Reversal of Myocardial Remodeling With Electrical Stimulation"; and U.S. Pat. No. 6,512,952 to Stahmann et al., entitled "Method And Apparatus For Maintaining Synchronized Pacing".

In view of the potential severity of heart failure, it is highly desirable to detect its onset within a patient and to track its progression or regression so that appropriate therapy can be provided. Many patients suffering from heart failure already have pacemakers or ICDs implanted therein or are candidates for such devices. Accordingly, it is desirable to provide such devices with the capability to automatically detect and track heart failure and, heretofore, a number of attempts have been made to monitor heart failure using implantable cardiac stimulation devices. For many patients with heart failure, the heart failure results in a generally higher heart rate for a given level of patient activity because of the poor pumping ability of the heart. More specifically, due to reduced stroke volume caused by heart failure, the heart must beat at a faster rate to meet the physiological demands of the patient. By equipping the implanted device with an activity sensor, the relationship between heart rate and activity can thereby be exploited to monitor heart failure.

See, for example, U.S. Pat. No. 6,190,324 to Kieval et al., entitled "Implantable Medical Device for Tracking Patient Cardiac Status", which describes an implantable medical device for monitoring CHF based on, inter alia, activity levels and heart rate. In one example, the ratio of heart rate to activity level is measured and used to monitor CHF. A potential disadvantage of the technique of Kieval et al., at least insofar as heart rate is concerned, is that the technique appears to detect and utilize the absolute heart rate of the patient. It is believed to be preferable to instead evaluate heart rate relative to the rest rate of the patient or relative to some measure of the heart rate reserve (HRR) of the patient (i.e. a measure of the difference between the rest rate and the maximum heart rate of the patient) so as to obtain a more useful measure of heart rate for the purposes of heart failure evaluation. Also, it appears that many of the exemplary techniques of Kieval et al. are directed to exploiting heart rate values obtained regardless of whether the patient is active or not. The present inventors have recognized that it is preferable to instead evaluate heart failure using heart rate values obtained only while the level of patient activity exceeds some predetermined minimum threshold, so as to permit a more effective evaluation of heart failure. In this regard, Kieval et al. mentions that capture of a heart rate activity coefficient (HRAC) value may be triggered based on either heart rate or activity levels. However, Kieval et al. does not appear to describe techniques that utilize any and all heart rate values obtained while patient activity exceeds a predetermined minimum. Instead, Kieval et al. describes, for example, the use of heart rate values obtained only within a specific range of activity level values.

Accordingly, it is desirable to provide techniques for automatically detecting and tracking heart failure based on patient heart rate and activity levels, which specifically take into account patient rest rate or HRR and which specifically exploit heart rate values measured only while the patient is active.

SUMMARY

In accordance with one embodiment, techniques are provided for evaluating heart failure within a patient using an implantable medical device. Briefly, values representative of heart rate and corresponding activity levels for the patient are detected during one or more periods of time when the patient is active. Activity-based cardiac fitness values are derived from the heart rate and the corresponding activity levels obtained during the periods of time when the patient is active, while also taking into account a predetermined patient rest rate. Heart failure, if any, within the patient is then evaluated based on the cardiac fitness values.

In an exemplary embodiment, a plurality of individual cardiac fitness values (R) are derived based on ratios of rest rate-adjusted heart rate values and corresponding activity level values detected while the patient is active. In one specific example, R is calculated using R=(Heart Rate−Rest Rate)/Activity Level. In another specific example, R is calculated using R=(Heart Rate−Rest Rate)/(HRR)/Activity Level, where HRR is set to HRR=(Maximum Heart Rate−Rest Rate). The maximum heart rate may be determined, for example, based on Maximum Heart Rate=220−Patient Age, or may be set based on an actual measured value for maximum patient heart rate obtained by a physician. In any case, all values of R obtained over a twenty-four hour period are used to populate a histogram (H). A numerical measure (M) of the histogram is then derived based, for example, on the centroid, mean, median or average of the histogram. Heart failure may then be detected by comparing the M against some predetermined threshold value indicative of the heart failure. The severity of heart failure may be evaluated by comparing M against a set of threshold values indicative of different levels of severity, which may be correlated with the aforementioned NYHA heart failure classes. A numerical value (L) representative of the lag, if any, between histograms may be obtained by comparing histograms obtained at different times. Any progression or regression in heart failure may then be tracked based on changes, if any, in L over time.

Thus, the ratios of individual rest-rate adjusted heart rate values and corresponding activity level values obtained during periods of time while the patient is active are used to provide a measure of heart failure. By using rest-rate adjusted heart rates rather than absolute heart rates, it is believed that a more useful measure of heart rate is exploited. In particular, changes in patient rest rate caused by, for example, any medications taken by the patient are thereby taken into account. By further taking into account HRR, the technique more effectively captures actual cardiac effort relative to both the patient's rest rate and the patient's maximum heart rate. Moreover, by utilizing any and all heart rate values obtained while the patient is active—rather than only using heart rate values obtained within some narrow range of activity or rather than using all heart rate values obtained regardless of activity—it is believed that a still more effective measure of heart failure is achieved. In this regard, the increase in heart rate required due to reduced stroke volume is most apparent while the patient is active and hence eliminating heart rate values detected while the patient is resting or is otherwise generally inactive provides for a more effective measure of heart failure.

Once heart failure is detected and evaluated, appropriate therapy is automatically provided by the implanted device, which may include CRT or drug therapy (if an implantable drug pump is provided with medication appropriate for heart failure.) If a significant change in heart failure is detected, appropriate warning signals are delivered to the patient, either via an implanted warning device (if so equipped) or via an external bedside monitor. In this manner, the patient is immediately alerted to any potentially life-threatening progression in heart failure so that immediate medical attention can be sought. Diagnostic information representative of the severity and progression of heart failure is also stored for subsequent review by the physician. Suitable diagnostic information may also be displayed via the bedside monitor.

Thus, various techniques are provided for use with implantable medical devices for detecting heart failure, tracking its progression, and for triggering appropriate therapy or warning signals. Other aspects, features and advantage will be apparent form the descriptions that follow.

BRIEF DESCRIPTION OF THE DRAWINGS

The above and further features, advantages and benefits will be apparent upon consideration of the present description taken in conjunction with the accompanying drawings, in which.

DETAILED DESCRIPTION OF THE PREFERRED EMBODIMENTS

The following description includes the best mode presently contemplated. This description is not to be taken in a limiting sense but is made merely to describe general principles of the illustrative embodiments. The scope of the invention should be ascertained with reference to the issued claims. In the description that follows, like numerals or reference designators are used to refer to like parts or elements throughout.

Overview of Implantable Heart Failure-Responsive System

Figure 1:
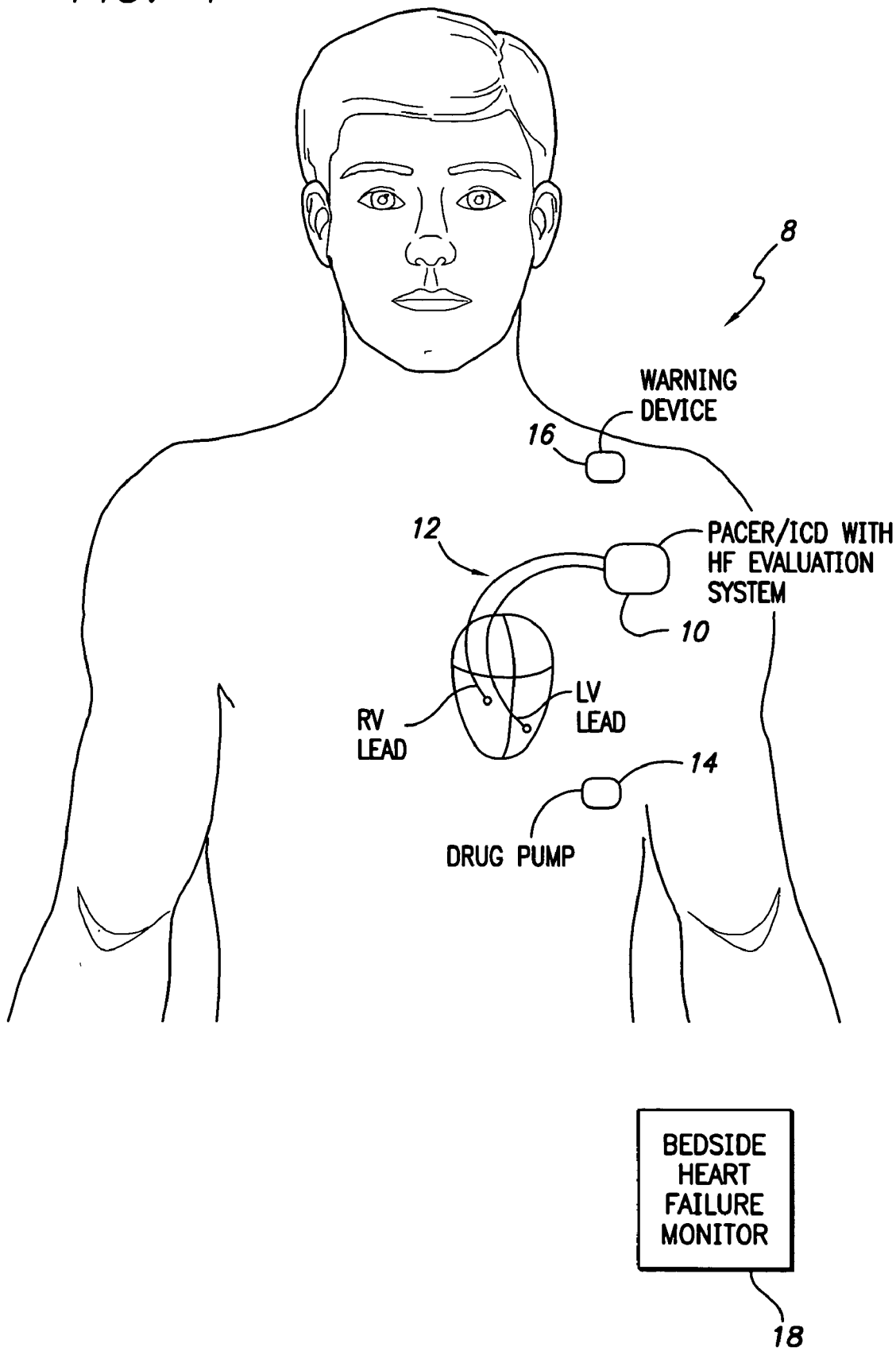
FIG. 1 illustrates pertinent components of an implantable heart failure-responsive medical system having a pacemaker or ICD capable of detecting heart failure and tracking its progression and further capable of delivering therapy or warning signals in response thereto.
Figure 4:
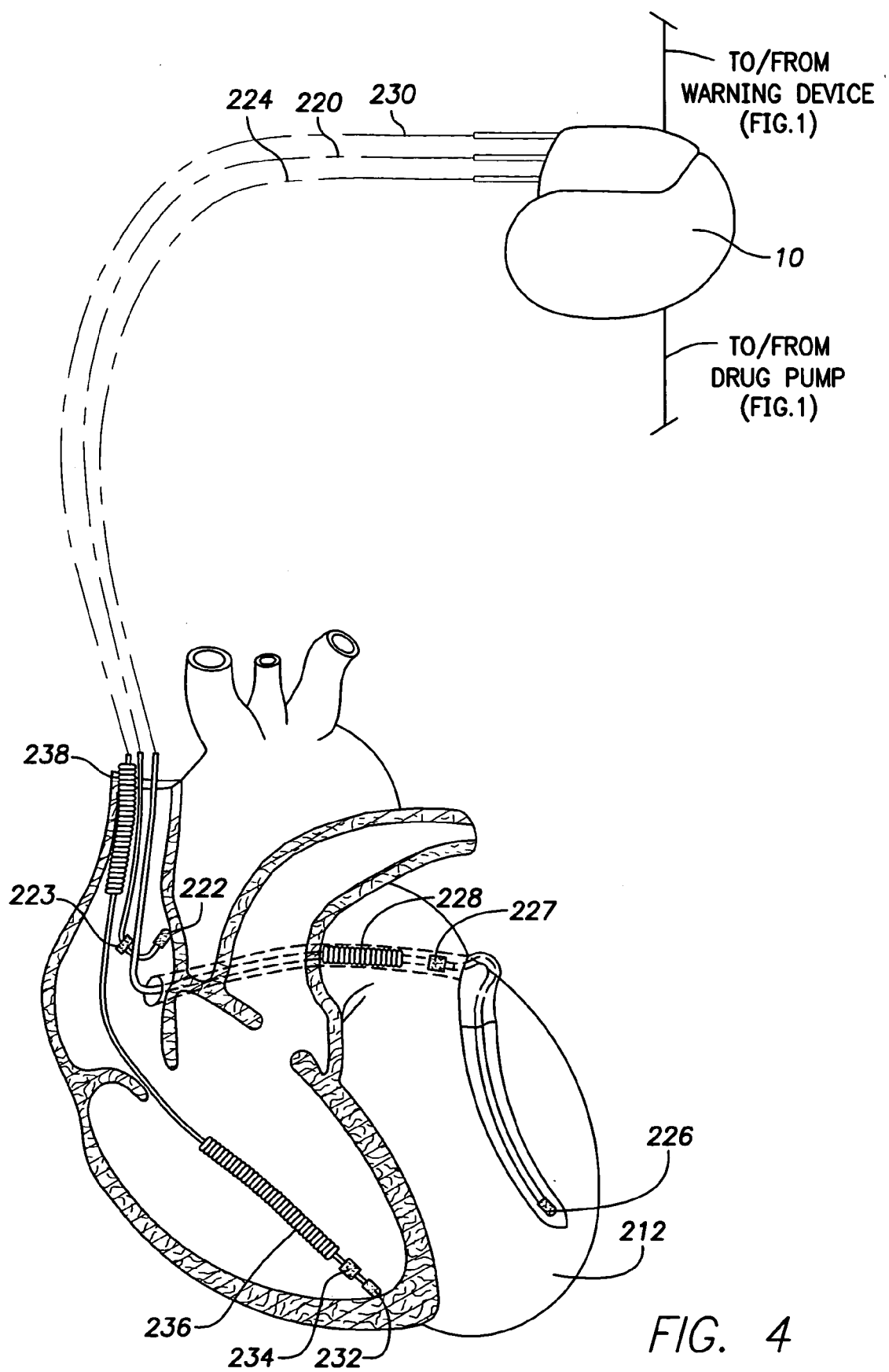
FIG. 4 is a simplified, partly cutaway view, illustrating the pacer/ICD of FIG. 1 along with full set of leads implanted into the heart of the patient.

FIG. 1 illustrates an implantable heart failure-responsive medical system 8 capable of detecting heart failure, determining its severity, tracking its progression and delivering appropriate warnings and therapy. Heart failure-responsive system 8 includes a pacer/ICD 10 or other cardiac stimulation device equipped with internal components for controlling the evaluation of heart failure and the delivery of therapy in response thereto. More specifically, pacer/ICD 10 receives electrical cardiac signals from at least two ventricular cardiac pacing/sensing leads 12 implanted within the heart of the patient (shown stylistically in phantom lines) from which patient heart rate is derived. In FIG. 1, only ventricular pacing leads are shown. A full set of pacing leads is shown in FIG. 4. The pacer/ICD also receives signals from an activity sensor, such as an accelerometer-based device, representative of the movement or activity of the patient. In the implementation of FIG. 1, the activity sensor is mounted within the implanted device (and is specifically shown within FIG. 5). In other implementations, the activity sensor is implanted elsewhere within the body. Implantable activity sensors are described in U.S. Pat. No. 6,002,963 to Mouchawar et al., entitled "Multi-Axial-Accelerometer-Based Sensor for an Implantable Medical Device and Method of Measuring Motion Measurements Therefor".

Based on patient heart rate and on the activity sensor signals, in combination with at least a previously stored patient heart rest rate value, the pacer/ICD detects heart failure, if present in the patient. The pacer/ICD also evaluates the severity of heart failure to, for example, identify the particular NYHA class of heart failure. The pacer/ICD also tracks the progression of heart failure. If heart failure is detected, appropriate therapy is automatically delivered by the implantable system under the control of the pacer/ICD. For example, CRT therapy may be delivered to the heart of the patient using the ventricular leads in an effort to improve cardiac function. Control parameters for CRT therapy are automatically adjusted based on the severity of the heart failure. Additionally, or in the alternative, the implantable system may be equipped with a drug pump 14 capable of the delivering drug therapy in an attempt to address heart failure. Discussions of possible medications for use in heart failure patients are provided below. Drug dosages provided by an implantable drug pump may be titrated based on the severity of heart failure.

Warning signals are generated using either an internal warning device 16 or an external bedside monitor 18 so as to notify the patient of the onset of heart failure or to advise the patient of any significant progression thereof. Internal warning device 16 may be a vibrating device or a "tickle" voltage device that, in either case, provides perceptible stimulation to the patient to alert the patient of any significant progression of heart failure so that the patient may immediately consult a physician. The bedside monitor provides audible or visual alarm signals to alert the patient as well as textual or graphic displays. In addition, once heart failure has been detected, diagnostic information is stored within the pacer/ICD for subsequent transmission to an external programmer (not shown in FIG. 1) for review by a physician or other medial professional. The physician may then prescribe any other appropriate therapies to address the heart failure. The physician may also adjust the operation of the pacer/ICD to activate, deactivate or otherwise control any therapies that are automatically applied. In addition, the bedside monitor may be directly networked with a centralized computing system for immediately notifying the physician of a significant increase in heart failure severity. Networking techniques for use with implantable medical systems are set forth, for example, in U.S. Pat. No. 6,249,705 to Snell, entitled "Distributed Network System for Use with Implantable Medical Devices."

Hence, FIG. 1 provides an overview of an implantable system for detecting heart failure, determining its severity, tracking its progression and delivering appropriate therapy. Individual systems may be implemented that do not necessarily perform all of these functions. For example, systems may be implemented that provide only for tracking the progression of heart failure within patients already known to have heart failure and for delivering suitable therapy. Other systems may be implemented, for example, that provide for detection of heart failure but not for evaluating of its severity or tracking its progression. In addition, suitable systems need not include all the components shown in FIG. 1. In many cases, for example, the system will include only the pacer/ICD and its leads, with heart failure therapy provided exclusively in the form of CRT. Drug pumps and warning devices are not necessarily implanted. Other implementations may employ an external monitor for generating warning signals but no internal warning device. These are just a few exemplary embodiments. No attempt is made herein to describe all possible combinations of components that may be provided in accordance with the general principles of the illustrative embodiments.

Also, note that internal signal transmission lines provided for interconnecting the various implanted components are not specifically shown in FIG. 1. Wireless signal transmission may alternatively be employed. In addition, the particular locations of the implanted components shown in FIG. 1 are merely illustrative and may not necessarily correspond to actual implant locations.

Overview of Activity-Based Heart Failure Evaluation Technique

Figure 2:
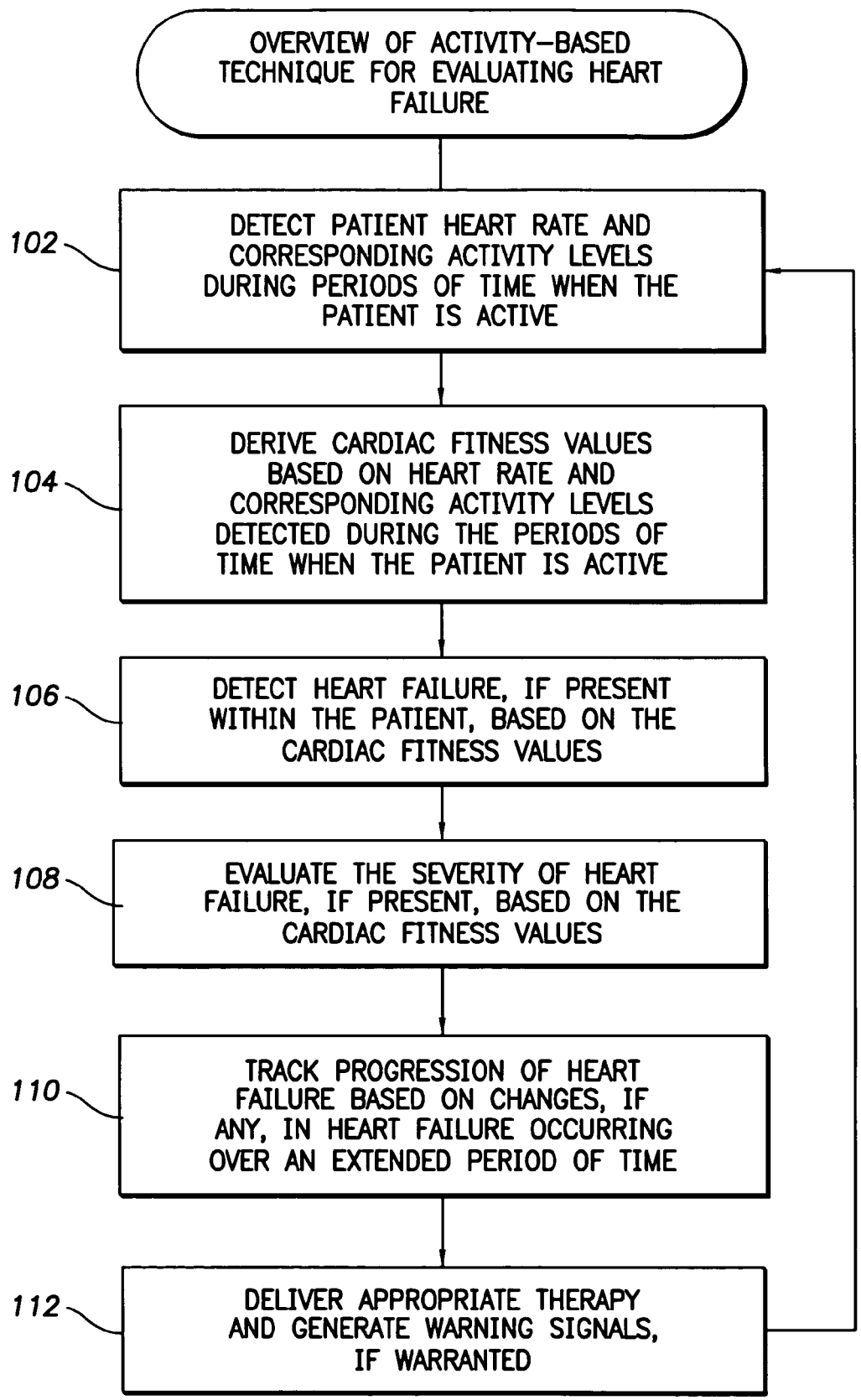
FIG. 2 is a flow diagram providing an overview of the method for evaluating heart failure performed by the system of FIG. 1.
Figure 3:
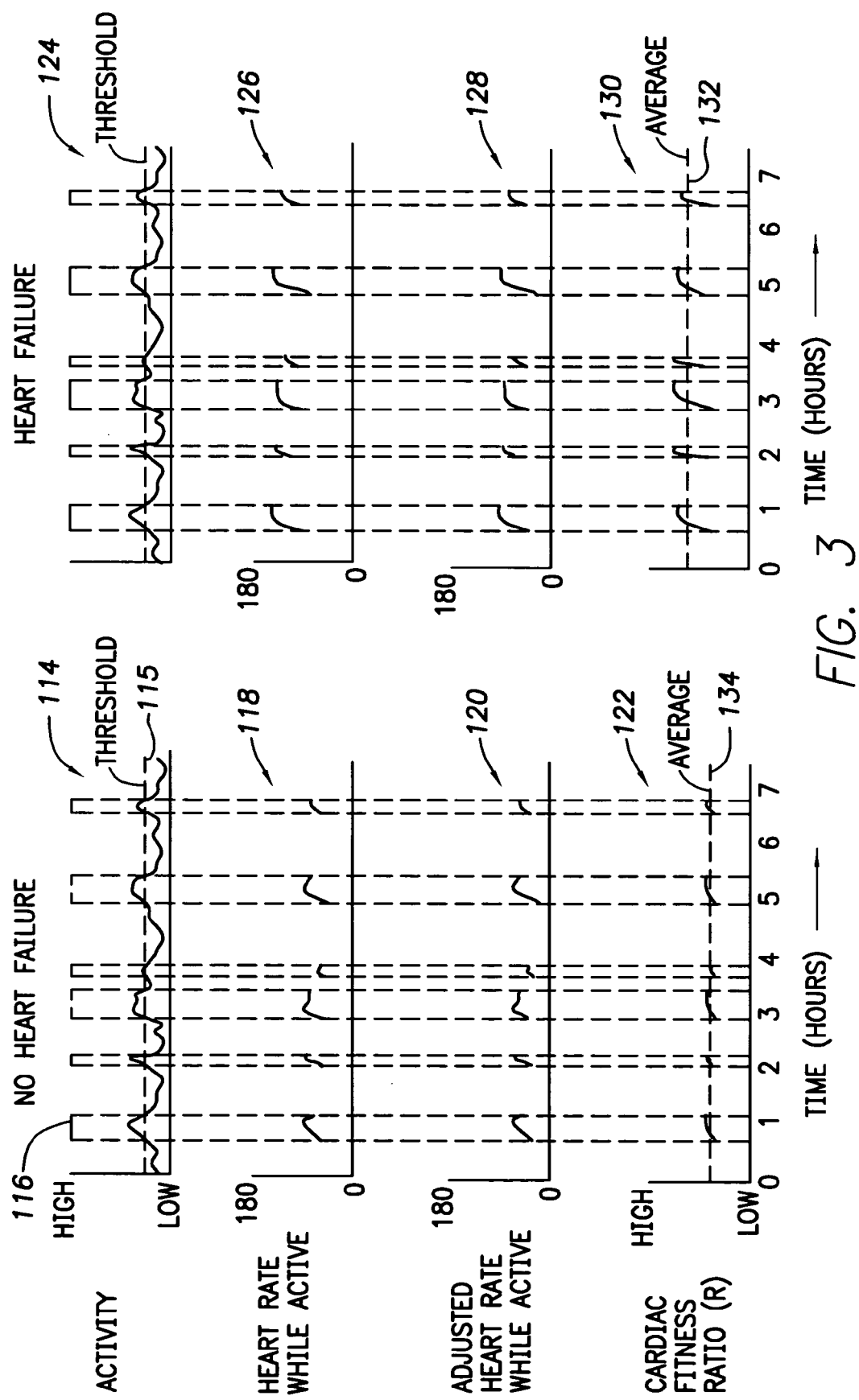
FIG. 3 sets forth stylized diagrams of exemplary heart rate, activity level, adjusted heart rate, and cardiac fitness ratio (R) values evaluated by the technique of FIG. 2 both for patients with heart failure and without heart failure.

FIGS. 2–3 summarize activity-based heart failure evaluation techniques that may be performed using the system of FIG. 1. Beginning with step 102, the pacer/ICD periodically detects and records patient heart rate values. The pacer/ICD also detects and records the corresponding activity levels of the patient, i.e. each time a heart rate value is detected and stored, the level of activity of the patient at that time is also detected and stored. Patient heart rate values and corresponding activity level values are only stored during periods of time when the patient is active (at least for the purposes of heart failure evaluation). To this end, activity levels may be compared against a predetermined threshold indicative of some minimum level of actively for the patient, such as the level of activity normally associated with walking. Heart rate values detected while the activity level of the patient remains below the threshold may used for other purposes. At step 104, the pacer/ICD then derives cardiac fitness values based on the heart rates and the corresponding activity levels obtained while the patient is active, while also taking into account patient rest rate. In one specific example, the cardiac fitness values are derived by subtracting the rest rate from the detected heart rate, then dividing by the corresponding activity level. In another example, the cardiac fitness values are derived while taking into account the HRR of the patient. These techniques are described more fully below. Other appropriate techniques may instead be used. The patient rest rate may be preprogrammed into the pacer/ICD and retrieved from memory or otherwise determined by the pacer/ICD. Techniques for determining patient rest rate are well known in the art.

At step 106, the pacer/ICD then detects heart failure, if present in the patient, based on the cardiac fitness values. Since cardiac fitness values are only generated based on detected heart rates obtained while the patient is active, the detection of heart failure is thereby based on data obtained only while the patient is active. At step, 108, the pacer/ICD then evaluates the severity of heart failure based on the cardiac fitness values. At step 110, the pacer/ICD tracks the progression of heart failure based on changes, if any, in heart failure occurring over an extended period of time. In examples described below, the pacer/ICD generates histograms of the cardiac fitness values for use in detecting heart failure, evaluating its severity and tracking its progression within steps 106–110. Other appropriate techniques may be exploited.

Once heart failure is evaluated, then at step 112, appropriate therapy and warning signals are delivered and diagnostic data is recorded by the pacer/ICD. As already explained, various types of therapy may be delivered, alone or in combination, depending upon the capabilities of the implanted system. For most patients, the severity of heart failure does not change significantly over short periods of time and so, once a determination has been made as to the current severity of heart failure, this determination need not the repeated, at least in the short-term. Accordingly, from many patients, once the severity of heart failure as been evaluated, it is sufficient to reevaluate the severity of heart failure only infrequently (e.g. every few weeks or months) to determine a change in status of the patient.

FIG. 3 includes various graphs illustrating patient activity levels, patient heart rate, and related parameters for exemplary patients with heart failure and without heart failure. The diagrams of FIG. 3 are stylized representations of hypothetical data provided to illustrate pertinent features of the illustrative embodiments. The graphs should not be construed as illustrating actual clinically-detected signals or parameters. Nor should the graphs be construed as representing heart rate characteristics of all heart failure patients. Referring first to graph 114, patient activity levels are shown (on an arbitrary scale from low to high) over a period of about seven hours for the exemplary patent without heart failure. As can be seen, the activity level varies significantly during the period of time. Peak levels of activity may correspond, for example, to periods of time when the patient is walking or running whereas the lowest levels of activity may corresponding, for example, to periods of time when the patient is resting. A minimum activity threshold 115 is shown within graph 114, which is indicative of the minimum level of activity needed to trigger collection of heart failure evaluation data. The threshold value is predetermined and may be specified, for example, by a physician programming the implanted system. The actual numerical value of the threshold will depend, in part, upon the particular range of values output from the specific activity sensor being used. In one example, the threshold is set to some percentage of the maximum numerical value expected to be provided by the activity sensor during vigorous exercise. For example, the activity threshold may be set to 25% of that value.

Periods of time during which the patient activity level exceeds the minimum threshold are illustrated by dashed lines 116. Graph 118 illustrates patient heart rate detected during those periods of time. As a practical matter, heart rate is continuously detected by the device. However, for the purposes of heart failure evaluation, only those heart rate values detected while the patient is active are used for heart failure evaluation. Graph 120 illustrates adjusted heart rate values during the periods of time when the patient is active. In the example of FIG. 3, the adjusted heart rate values are derived simply by subtracting the rest heart rate of the patient (not specifically shown) from the detected heart rate values. Other techniques for adjusted the detected heart rate based on rest rate alone or in combination with other factors may be alternatively be employed. Graph 122 illustrates cardiac fitness ratio values (R) calculated based on data obtained during the periods of time while the patient is active. The cardiac fitness ratio, in this example, is the adjusted heart rate divided by the corresponding activity level (shown on an arbitrary scale from low to high.) Actual numerical values for the cardiac fitness ratio R will depend upon the particular numerical values output by the activity sensor. Note that, if the activity sensor is configured to output individual activity level values of zero, the activity values should be a rescaled to provide for a minimum, nonzero value so as to avoid any possible "divide by zero" errors.

As can be seen from graph 122, the cardiac fitness ratio values are relatively uniform during the periods of time in which patient is active for the patient without heart failure. As long as heart failure is not present, the heart usually responds promptly to changes in patient activity levels so as to provide the minimum heart rate necessary to sustain the patient during exercise. This is in contrast with cardiac fitness ratios for many patients with heart failure, shown by way of corresponding graphs on the right side of FIG. 3. Briefly, graphs 124, 126, 128 and 130 illustrate, respectively, activity level, heart rate, adjusted heart rate, and cardiac fitness ratio (R) values for an exemplary patient with heart failure wherein heart failure has resulted in a reduction in stroke volume but wherein the heart is still capable of beating at a fairly high rate. (Note that, if heart failure becomes too severe, the heart can lose its ability to increase its pumping rate in response to exercise, primarily as a result of an overload of catecholamines. The exemplary heart failure patient of FIG. 3 has not reached that level of severity.)

In the example of FIG. 3, the cardiac fitness ratio values are generally higher for the exemplary heart failure patient than the exemplary non-heart failure patient for the same level of activity because the heart must beat at a higher rate, due to reduced stroke volume, to provide sufficient blood flow to the body to sustain the patient during exercise. As a result, an average of the cardiac fitness ratio values (shown by way of line 132) obtained during periods of time while the patient is active is higher for the exemplary heart failure patient than a corresponding average obtained for the exemplary non-heart failure patient (and shown by way of line 134). Thus, cardiac fitness ratio values obtained for periods of time while the patient is active can be used to detect heart failure, evaluate its severity, and track its progression, etc. Although not specifically shown in FIG. 3, one or more cardiac fitness ratio thresholds may be set. The average value for the cardiac fitness ratio obtained for a particular patient is then compared against the predetermined threshold to detect heart failure, evaluate its severity, and track its progression. Techniques using histograms generated based on the cardiac fitness ratio values are described below.

Hence, FIG. 3 highlights certain features of the technique of FIG. 2, particularly the use of adjusted heart rate values obtained only during periods of time while the patient is active. By isolating the periods of time while the patient is active, heart failure may be evaluated more effectively than if heart rate and activity values were tracked at all times, including periods of time while the patient is resting or is sleep. By utilizing adjusted heart rate values derived, in part, based upon rest rate, the method automatically compensates for possible variations in patient rest rate. If absolute heart rate were instead used, then changes in rest rate caused by medications or the like, could otherwise affect the heart failure evaluation, potentially yielding erroneous results.

Note that the graphs of FIG. 3 illustrate identical activity patterns for both the heart failure patient and the non-heart failure patient, i.e. graphs 114 and 124 are the same. In practice, due to the debilitating effects of heart failure, a patient with heart failure is less likely to be active and hence there will typically be fewer periods of time when the active level exceeds the minimum activity threshold. Hence, fewer cardiac fitness ratio data points will likely be obtained during a given day for a heart failure patient than for a non-heart failure patient. Nevertheless, by examining the average of the cardiac fitness ratio values that have been obtained (or by evaluating some corresponding numerical measure based on a cardiac fitness histogram), heart failure can still be reliably detected. One of the reasons that the illustrative embodiment utilizes heart rate values obtained only during periods of time while patient activity level exceeds a minimum threshold is to automatically compensate for the general reduction in average activity levels caused by heart failure. If all heart failure values were instead used (regardless of patient activity level), then the data obtained for heart failure patients could be skewed toward lower cardiac fitness ratio values associated with rest, thus making it more difficult to reliably detect heart failure based on the data. Note also that any medications (or other factors) that serve to compensate for heart failure may improve stroke volume and thereby reduce the extent to which the heart rate is elevated during exercise. Stroke volume is also affected by the general level of fitness or conditioning of a person. The physician should take such factors into account in evaluating any warnings provided by the implanted device and in programming the device to provide responsive therapy.

In the following section, an exemplary pacer/ICD will be described, which includes specific components for implementing the heart failure evaluation technique of FIGS. 2–3.

Exemplary Pacer/ICD

Figure 5:
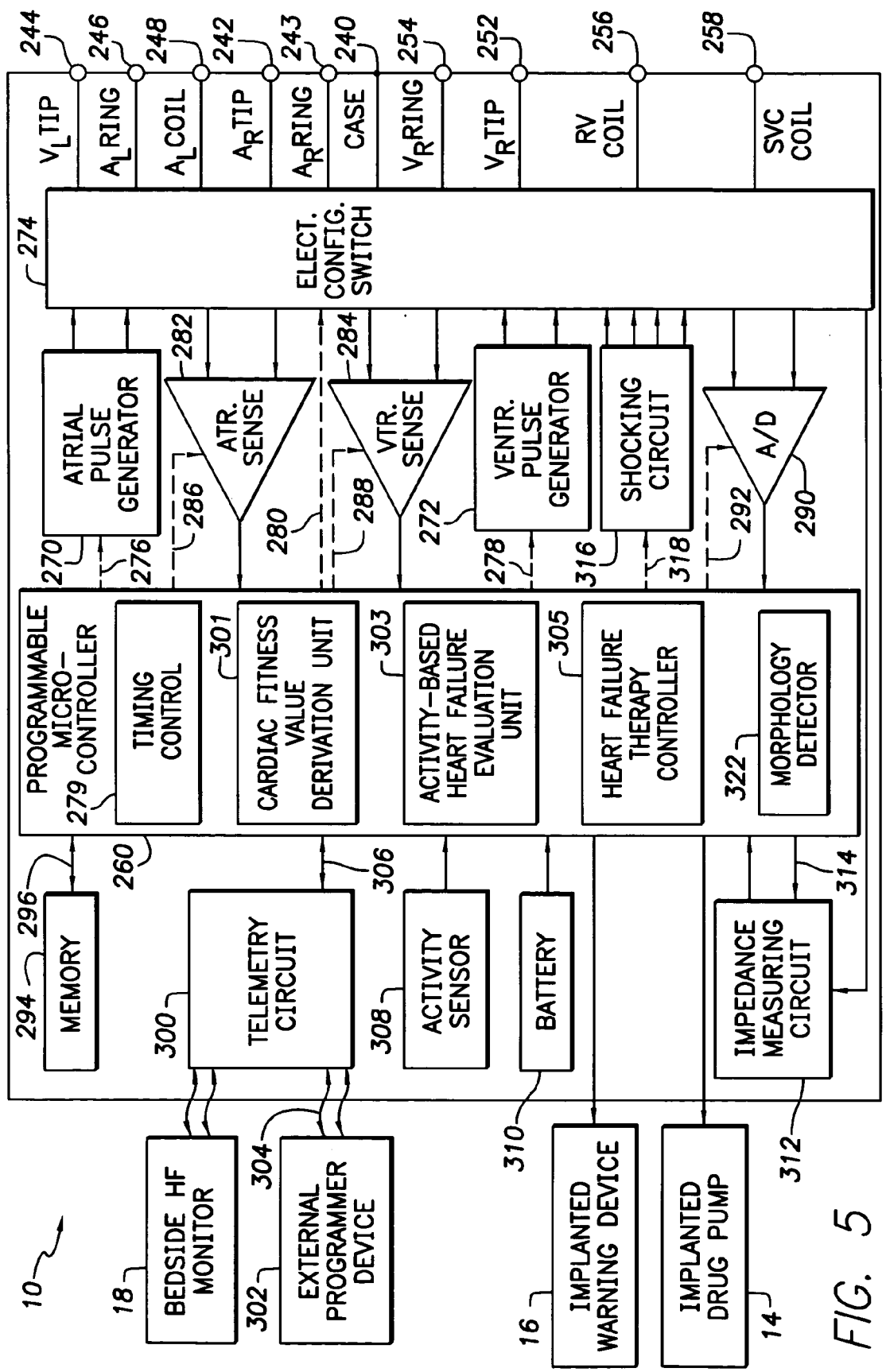
FIG. 5 is a functional block diagram of the pacer/ICD of FIG. 4, illustrating basic circuit elements that provide cardioversion, defibrillation and/or pacing stimulation in the heart and particularly illustrating components for detecting heart failure and tracking its progression and for controlling delivery of therapy or warning signals in response thereto.

With reference to FIGS. 4 and 5, a detailed description of an exemplary pacer/ICD for use with the system of FIG. 1 will now be provided. FIG. 4 provides a simplified block diagram of the pacer/ICD, which is a dual-chamber stimulation device capable of treating both fast and slow arrhythmias with stimulation therapy, including cardioversion, defibrillation, and pacing stimulation, as well as capable of detecting heart failure, evaluating its severity, tracking the progression thereof, and controlling the delivery of therapy and warnings in response thereto.

To provide atrial chamber pacing stimulation and sensing, pacer/ICD 10 is shown in electrical communication with a heart 212 by way of a left atrial lead 220 having an atrial tip electrode 222 and an atrial ring electrode 223 implanted in the atrial appendage. Pacer/ICD 10 is also in electrical communication with the heart by way of a right ventricular lead 230 having, in this embodiment, a ventricular tip electrode 232, a right ventricular ring electrode 234, a right ventricular (RV) coil electrode 236, and a superior vena cava (SVC) coil electrode 238. Typically, the right ventricular lead 230 is transvenously inserted into the heart so as to place the RV coil electrode 236 in the right ventricular apex, and the SVC coil electrode 238 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 224 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 224 is designed to receive atrial and ventricular cardiac signals and to deliver left ventricular pacing therapy using at least a left ventricular tip electrode 226, left atrial pacing therapy using at least a left atrial ring electrode 227, and shocking therapy using at least a left atrial coil electrode 228. With this configuration, biventricular pacing can be performed. Although only three leads are shown in FIG. 4, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 10 is shown in FIG. 5. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 240 for pacer/ICD 10, shown schematically in FIG. 5, is often referred to as the "can", "case" or "case electrode" and may be programmably selected to act as the return electrode for all "unipolar" modes. The housing 240 may further be used as a return electrode alone or in combination with one or more of the coil electrodes, 228, 236 and 238, for shocking purposes. The housing 240 further includes a connector (not shown) having a plurality of terminals, 242, 243, 244, 246, 248, 252, 254, 256 and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 222 and a right atrial ring ($A_R$ RING) electrode 243 adapted for connection to right atrial ring electrode 223. To achieve left chamber sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection to the left ventricular ring electrode 226, the left atrial tip electrode 227, and the left atrial coil electrode 228, respectively. To support right chamber sensing, pacing and shocking, the connector further includes a right ventricular tip terminal ($V_R$ TIP) 252, a right ventricular ring terminal ($V_R$RING) 254, a right ventricular shocking terminal ($R_V$ COIL) 256, and an SVC shocking terminal (SVC COIL) 258, which are adapted for connection to the right ventricular tip electrode 232, right ventricular ring electrode 234, the RV coil electrode 236, and the SVC coil electrode 238, respectively.

At the core of pacer/ICD 10 is a programmable microcontroller 260, which controls the various modes of stimulation therapy. As is well known in the art, the microcontroller 260 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design and operation of the microcontroller 260 are not critical. Rather, any suitable microcontroller 260 may be used that carries out the functions described herein. The use of microprocessor-based control circuits for performing timing and data analysis functions are well known in the art.

As shown in FIG. 5, an atrial pulse generator 270 and a ventricular pulse generator 272 generate pacing stimulation pulses for delivery by the right atrial lead 220, the right ventricular lead 230, and/or the coronary sinus lead 224 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry (not separately shown) used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. Switch 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 282 and ventricular sensing circuits 284 may also be selectively coupled to the right atrial lead 220, coronary sinus lead 224, and the right ventricular lead 230, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers or shared amplifiers. The switch 274 determines the "sensing polarity" of the cardiac signal by selectively closing the appropriate switches, as is also known in the art. In this way, the clinician may program the sensing polarity independent of the stimulation polarity. Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity in the appropriate chambers of the heart.

For arrhythmia detection, pacer/ICD 10 utilizes the atrial and ventricular sensing circuits, 282 and 284, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 260 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 290. The data acquisition system 290 is configured to acquire intracardiac electrogram signals, convert the raw analog data into a digital signal, and store the digital signals for later processing and/or telemetric transmission to an external device 302. The data acquisition system 290 is coupled to the right atrial lead 220, the coronary sinus lead 224, and the right ventricular lead 230 through the switch 274 to sample cardiac signals across any pair of desired electrodes. The microcontroller 260 is further coupled to a memory 294 by a suitable data/address bus 296, wherein the programmable operating parameters used by the microcontroller 260 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 294 through a telemetry circuit 300 in telemetric communication with the external device 302, such as a programmer, transtelephonic transceiver or a diagnostic system analyzer. The telemetry circuit 300 is activated by the microcontroller by a control signal 306. The telemetry circuit 300 advantageously allows intracardiac electrograms and status information relating to the operation of pacer/ICD 10 (as contained in the microcontroller 260 or memory 294) to be sent to the external device 302 through an established communication link 304. Pacer/ICD 10 further includes an accelerometer or other physiologic sensor 308, commonly referred to as a "rate-responsive" sensor because it is typically used to adjust pacing stimulation rate according to the exercise state of the patient. However, the physiological sensor 308 may further be used to detect changes in cardiac output, changes in the physiological condition of the heart, or diurnal changes in activity (e.g., detecting sleep and wake states) and to detect arousal from sleep. Accordingly, the microcontroller 260 responds by adjusting the various pacing parameters (such as rate, AV Delay, V—V Delay, etc.) at which the atrial and ventricular pulse generators, 270 and 272, generate stimulation pulses. While shown as being included within pacer/ICD 10, it is to be understood that the physiologic sensor 308 may also be external to pacer/ICD 10, yet still be implanted within or carried by the patient. A common type of rate responsive sensor is an activity sensor incorporating an accelerometer or a piezoelectric crystal, which is mounted within the housing 240 of pacer/ICD 10. Other types of physiologic sensors are also known, for example, sensors that sense the oxygen content of blood, respiration rate and/or minute ventilation, pH of blood, ventricular gradient, etc. However, any sensor may be used which is capable of sensing a physiological parameter that corresponds to the exercise state of the patient an, in particular, is capable of detecting arousal from sleep or other movement.

The pacer/ICD additionally includes a battery 310, which provides operating power to all of the circuits shown in FIG. 5. The battery 310 may vary depending on the capabilities of pacer/ICD 10. If the system only provides low voltage therapy, a lithium iodine or lithium copper fluoride cell may be utilized. For pacer/ICD 10, which employs shocking therapy, the battery 310 must be capable of operating at low current drains for long periods, and then be capable of providing high-current pulses (for capacitor charging) when the patient requires a shock pulse. The battery 310 must also have a predictable discharge characteristic so that elective replacement time can be detected. Accordingly, pacer/ICD 10 is preferably capable of high voltage therapy and appropriate batteries.

As further shown in FIG. 5, pacer/ICD 10 is shown as having an impedance measuring circuit 312 which is enabled by the microcontroller 260 via a control signal 314. Uses of the an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 260 further controls a shocking circuit 316 by way of a control signal 318. The shocking circuit 316 generates shocking pulses of low (up to 0.5 joules), moderate (0.5–10 joules) or high energy (11 to 40 joules), as controlled by the microcontroller 260. Such shocking pulses are applied to the heart of the patient through at least two shocking electrodes, and as shown in this embodiment, selected from the left atrial coil electrode 228, the RV coil electrode 236, and/or the SVC coil electrode 238. The housing 240 may act as an active electrode in combination with the RV electrode 236, or as part of a split electrical vector using the SVC coil electrode 238 or the left atrial coil electrode 228 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 260 is capable of controlling the synchronous or asynchronous delivery of the shocking pulses.

Microcontroller 260 also includes various components directed to the controlling the detection and treatment of heart failure. More specifically, the microcontroller includes a cardiac fitness value derivation unit 301, which derives cardiac fitness values from heart rate and corresponding activity levels detected during periods of time while the patient is active while also taking into account the patient rest rate. Activity levels are derived from data provided by activity sensor 308. Patient heart rate is calculated by other components of the microprocessor based on signals received from the sense amplifiers. Rest rate is retrieved from memory 294. The microcontroller also includes an activity-based heart failure evaluation unit 303, which processes the cardiac fitness values to detect heart failure, determine its severity, and track its progression. Additionally, the microcontroller includes a heart failure therapy controller 305 for controlling the delivery therapy and/or warning signals based upon the heart failure evaluation. In particular, the heart failure therapy controller generates appropriate control signals for controlling implanted drug pump 14, implanted warning device 16 and external bedside monitor 18. The therapy controller also generates appropriate signals for forwarding to other components of the microcontroller for controlling pacing therapy based upon heart failure, such as for controlling CRT. In additional, the heart failure controller stores appropriate diagnostic information in memory 292 such as data specifying the severity of any heart failure detected and the types of therapy employed in response thereto. The operation of these components will be described in greater detail below with reference to the remaining figures.

Depending upon the particular implementation, the various components of the microcontroller may be implemented as separate software modules. The modules may be combined to permit a single module to perform multiple functions. In addition, although shown as being sub-components of the microcontroller, some or all of these components may be implemented separately from the microcontroller.

Exemplary Heart Failure Evaluation Technique Using Histogram-Based Techniques

Referring to the remaining figures, an exemplary heart failure evaluation technique will be described wherein histogram-based techniques are exploited. Referring first FIG. 6, at step 400, the pacer/ICD retrieves values representative of patient heart rest rate along with predetermined threshold values including a minimum activity threshold and various heart failure severity thresholds. These values may be initially specified by physician during programming of the implanted device then stored in internal memory. Beginning at step 402, a 24-hour timer is activated so as to time collection of pertinent heart rate and activity data over a 24-hour period. The point during the day when the timer is activated is arbitrary and may be set, for example, to begin exactly at midnight. In any case, at step 404, the current heart rate and the current activity level of the patient are detected. So long as the current activity level remains below the minimum activity threshold, step 404 is periodically repeated, for example, every 30 seconds. However, once the activity level exceeds the minimum threshold then step 406 is performed wherein the pacer/ICD calculates a cardiac fitness ratio R based upon, at least, heart rate, rest rate, and activity level using one of the following formulas:

$$R = (\text{Heart Rate} - \text{Rest Rate})/\text{Activity Level}$$

or $$R = ((\text{Heart Rate} - \text{Rest Rate})/HRR)/\text{Activity Level} * 100$$

where HRR is (Heart Rate Max−Rest Rate).

In the first example, heart rate is first adjusted by subtracting rest rate, and then divided by the corresponding activity level to obtain R. In the second example, heart rate is first adjusted based upon rest rate, then divided by both HRR and activity level to obtain R. Herein, HRR is the difference between a maximum heart rate for the particular patient and the rest rate for the particular patient. Maximum heart rate may be calculated based upon 220 minus patient age or may be derived using other techniques or may be simply programmed by the physician. In the second example, a factor of 100 is employed to scale the resulting cardiac fitness ratio values in the range of 0.0 and 1.0. This is arbitrary.

Specific examples using the first formula are provided in TABLE I. All heart rates are in beats per minute (bpm). Activity levels are scaled between 1–100, i.e. the actual numerical values provided by the active sensor (which are representative of patient activity level) are first scaled between 1–100. Among other advantages, this prevents "divide by zero" calculation problems.

TABLE I

| Detected Heart Rate | Rest Rate | Adjusted Heart Rate | Activity Level | Cardiac Fitness Ratio (R) |
|---|---|---|---|---|
| 110 | 80 | 30 | 75 | 0.4 |
| 90 | 80 | 10 | 25 | 0.4 |
| 80 | 80 | 0 | 10 | 0.0 |
| 160 | 80 | 80 | 100 | 0.8 |

Specific examples using the second formula are provided in TABLE II.

TABLE II

| Detected Heart Rate | Max. Heart Rate | Rest Rate | HRR Adjusted Heart Rate | Activity Level | Cardiac Fitness Ratio (R) |
|---|---|---|---|---|---|
| 110 | 160 | 80 | 0.375 | 75 | 0.5 |
| 90 | 160 | 80 | 0.125 | 25 | 0.5 |
| 80 | 160 | 80 | 0.0 | 10 | 0.0 |
| 160 | 160 | 80 | 1.0 | 100 | 1.0 |

As can be seen, somewhat different values for the cardiac fitness ratio are generated depending upon the particular formula used. Accordingly, different values for the various threshold values are preferably used. Routine experimentation may be performed to identify appropriate threshold values for use with either formula. Whether the device uses the first formula or the second formula depends upon the particular programming of the device. It is anticipated that most devices will be programmed with one formula or the other, but not both. In addition, as noted, other formulas for calculating cardiac fitness values based upon heart rate, rest rate and activity levels other factors may alternatively be employed. In general, it is desirable to employ a formula that helps to emphasize the increase in heart rate over rest rate so as to automatically compensate for changes in rest rate, which may be triggered as a result of medications or changes in the anatomy or physiology of the patient, including changes brought on by heart failure itself. Other formulas for calculating the cardiac fitness values may include, for example, formulas based on metabolic equivalent (MET). See, for example, *Clinical Cardiac Pacing*, by Ellenbogen et al., W B Saunders, 1995, pages 434–436.

Figure 6:
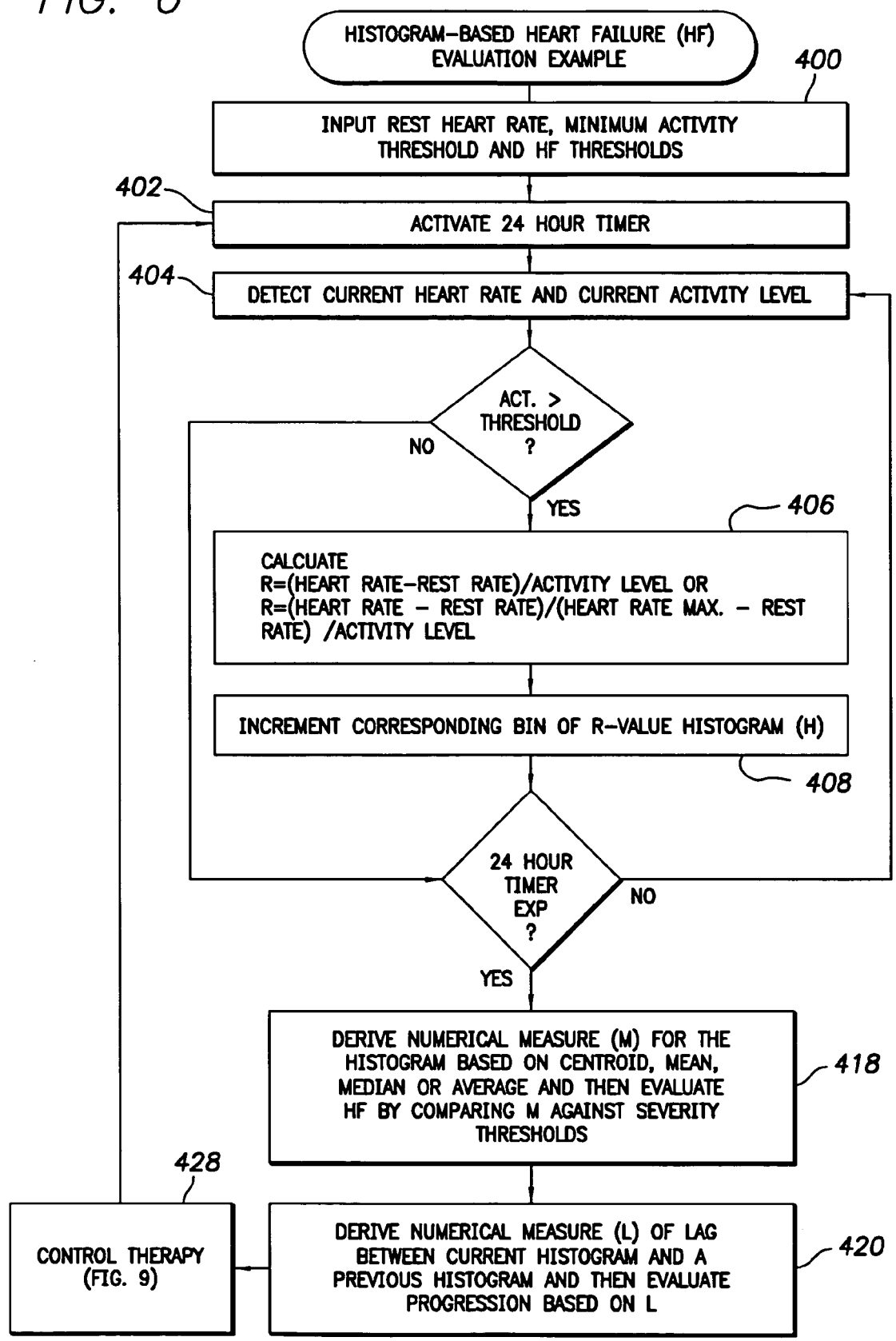
FIG. 6 is a flow diagram illustrating a particular exemplary technique performed by the implanted system of FIGS. 4–5 for evaluating heart failure based on rest-rate adjusted heart rate values and corresponding activity levels, which exploits histogram techniques.
Figure 7:
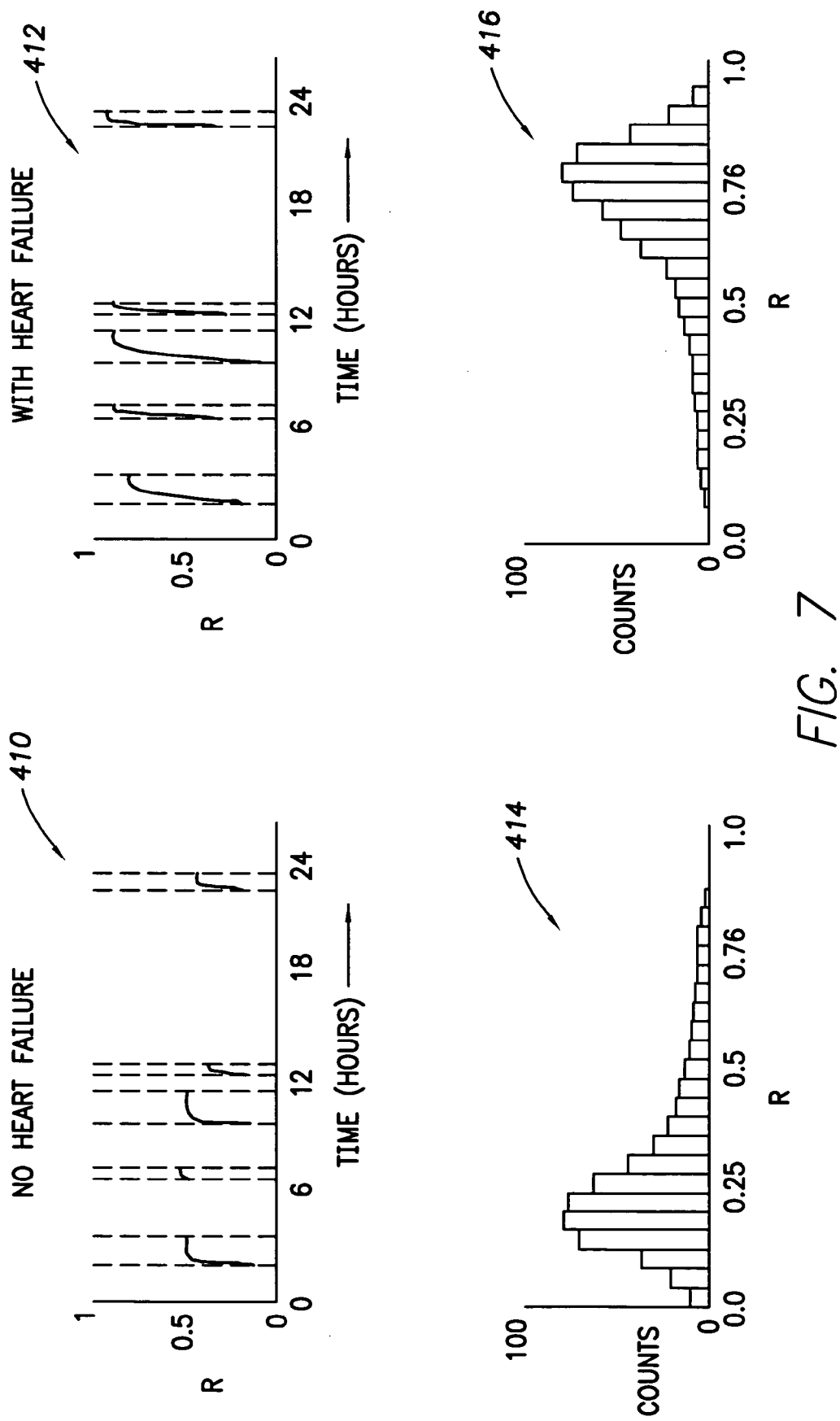
FIG. 7 sets forth stylized diagrams of exemplary cardiac fitness ratios (R) and corresponding histograms evaluated using the techniques of FIG. 6 both for patients with heart failure and without heart failure.

At step 408 of FIG. 6, the pacer/ICD then increments a corresponding bin of an R-value histogram (H). In other words, various ranges of values of the cardiac fitness ratio R are specified and, whenever a value of R is found to be within one of those arranges, a counter associated with the range is incremented. Steps 404–408 are repeated periodically until the 24-hour timer expires. Exemplary cardiac fitness ratio graphs and corresponding resulting histograms for a 24-hour period are shown within FIG. 7. As with FIG. 3 above, FIG. 7 provides separate graphs for a patient with heart failure and a patient without heart failure. The graphs of FIG. 7 are stylized representations provided to illustrate pertinent features of illustrative embodiments and should not be construed as being representative of clinically-detected values. In a first graph 410, cardiac fitness ratio values R, scaled between zero and one, are shown for a patient without heart failure obtained during periods of time wherein patient activity exceeds a minimum activity threshold. In a second graph 412, cardiac fitness ratio values R, also scaled between zero and one, are shown for the patient with heart failure, again only during periods of time wherein patient activity exceeds the minimum activity threshold. As can be seen, the cardiac fitness ratio is generally quite a bit higher for the heart failure patient then for the non-heart failure patient. (Within FIG. 7, the individual heart rate values, adjusted heart rate values, and activity values are not shown, only the resulting scaled cardiac fitness ratios. Refer to FIG. 3 for examples of the former.)

As noted, individual cardiac fitness ratio values R obtained over the 24-hour period are used to populate corresponding histograms. This is illustrated by exemplary histograms 414 and 416. Histogram 414 illustrates exemplary count totals obtained over the 24-hour period for a patient without heart failure; whereas histogram 416 illustrates exemplary count totals also obtained over a 24-hour period for the patient with heart failure. As can be seen, histogram 414 is generally skewed towards lower cardiac fitness ratio values whereas histogram 416 is generally skewed towards higher cardiac fitness ratio values. As already explained, due to reduced stroke volume within many heart failure patients, the heart rate during exercise must be greater in order to satisfy the needs of the patient and, as a result, a higher ratio of adjusted heart rate to activity level is found within such patients, at least during exercise. Hence, the histogram of cardiac fitness ratio values obtained during activity is likewise skewed to higher values, at least after a sufficient number of values are obtained, such as over a 24-hour period.

Returning and now to FIG. 6, at step 418, the pacer/ICD derives a numerical value (M) for the histogram representative of the centroid, mean, medium or average of histogram (or other suitable value), calculated using otherwise conventional techniques. Also at step 418, the pacer/ICD evaluates heart failure with the patient by comparing M against the heart failure thresholds initially input at step 400. To this end, M may be compared against a single threshold indicative the presence of heart failure to thereby detect the onset of heart failure. Thereafter, M may be compared against a set of different threshold values representative of various levels of severity of heart failure. Exemplary values are set forth in TABLE III. These values are provided merely for purposes of illustration. Actual values may be specified by the physician or may be generated by the pacer/ICD based upon data input by the physician. Clinical studies may be performed using routine experimental techniques to identify ranges of values of M associated with different levels of heart failure. Although only four classifications are show in the table, the severity of heart failure may be further subdivided into a greater number of classification levels.

TABLE III

| M | Heart Failure Severity |
|---|---|
| 0.0–0.25 | No Heart Failure |
| 0.25–0.50 | Mild |
| 0.50–0.75 | Moderate |
| 0.75–1.00 | Severe |

Then, at step 420, the pacer/ICD derives a numerical measure (L) representative of a lag between the latest histogram and a previously calculated and stored histogram so as to evaluate the progression of heart failure. In one example, the current histogram calculated based on data from the most recent 24-hour period is compared at step 420 against the histogram of the previous 24-hour period.

In one example, the lag value (L) is calculated by finding the value of L that yields a maximum value for $S_L$:

$$S_L = \sum_{i=-N}^{+N} H_{TODAY}(i) * H_{YESTERDAY}(i-L) \quad (1)$$

In other words, $S_L$ is calculated using Equation (1) for different integer values of L until a maximum value of $S_L$ is found. Otherwise conventional algorithms may be employed for identifying the value of L that yields a maximum of $S_L$. In equation (1), $H_{TODAY}$ represents the latest histogram H, i.e. the histogram obtained from data collected over the most recent 24-hour period. $H_{YESTERDAY}$ represents the histogram from the previous 24-hour period. Other suitable techniques may instead be employed for calculating lag values between the two histograms or between sets of two or more histograms. In general, any of a variety of numerical techniques may be employed that quantify a difference between present and previous histograms in such as way as to permit tracking of heart failure. For example, the current histogram can be compared against an average histogram derived from all previous histograms obtained for that same patient. In other words, a "running average" cardiac fitness histogram is maintained for the patient. Note also that, during a first iteration of FIG. 6, step 420 is skipped since no previous histogram has yet been generated.

Figure 8:
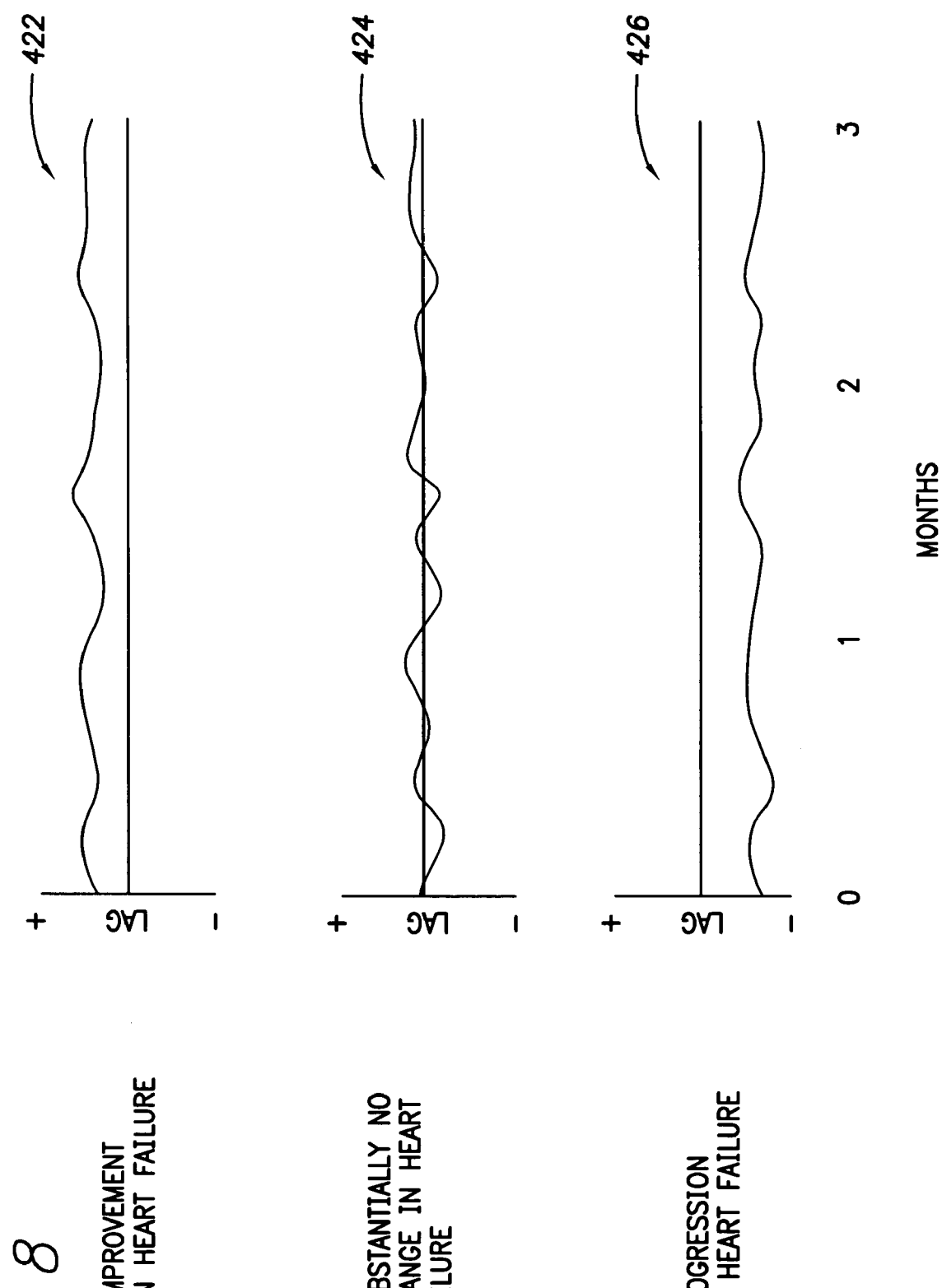
FIG. 8 sets forth stylized diagrams of exemplary histogram lag values (L) illustrating (a) an improvement in heart failure, (b) a progression of heart failure and (c) a lack of change in heart failure, as determined using the techniques of FIG. 6.

Using the lag technique, a generally positive lag value is indicative of an improvement or regression in heart failure whereas a generally negative lag value is representative of a progression or worsening of heart failure. So long as the lag value remains substantially near zero, status quo is maintained. This is illustrated in FIG. 8. Briefly, a first graph 422 illustrates lag values obtained over a period of three months for a patient in which heart failure is improving. As can be seen, lag values are generally positive. A second graph 424 illustrates lag values for a patient in which heart failure is remaining substantially the same. Finally, a third graph 426 illustrates lag values obtained for patient in which heart failure is steadily progressing. As with the other figures provided with this patent application, the graphs of FIG. 8 are merely stylized representations provided to illustrate pertinent features of the illustrative embodiments and should not be construed as being indicative of actual clinically-detected values.

As already noted, any medications (or other factors) that serve to compensate for heart failure may reduce the extent to which the heart rate is elevated during exercise. The physician should take such factors into account in evaluating any warnings provided by the implanted device and in programming the device to provide responsive therapy. In particular, any factors that tend to compensate for heart failure may affect the values obtained for M and L and should be taken into account by the physician. For example, should the lag values L indicate a possible regression of heart failure, the physician should evaluate the patient using otherwise conventional diagnostic techniques to verify that the lag value represents a true improvement in the health of the patient. Also, as already noted, when heart failure become particularly severe, the heart can lose its ability to increase its pumping rate in response to exercise due to an overload of catecholamines. This may result in a decrease in values for M and a corresponding change in L. This should not be misconstrued as representing an improvement in the health of the patient.

Finally, returning to FIG. 6, at step 428, the pacer/ICD delivers appropriate therapy or warning signals based upon heart failure, if any, that has been detected.

Figure 9:
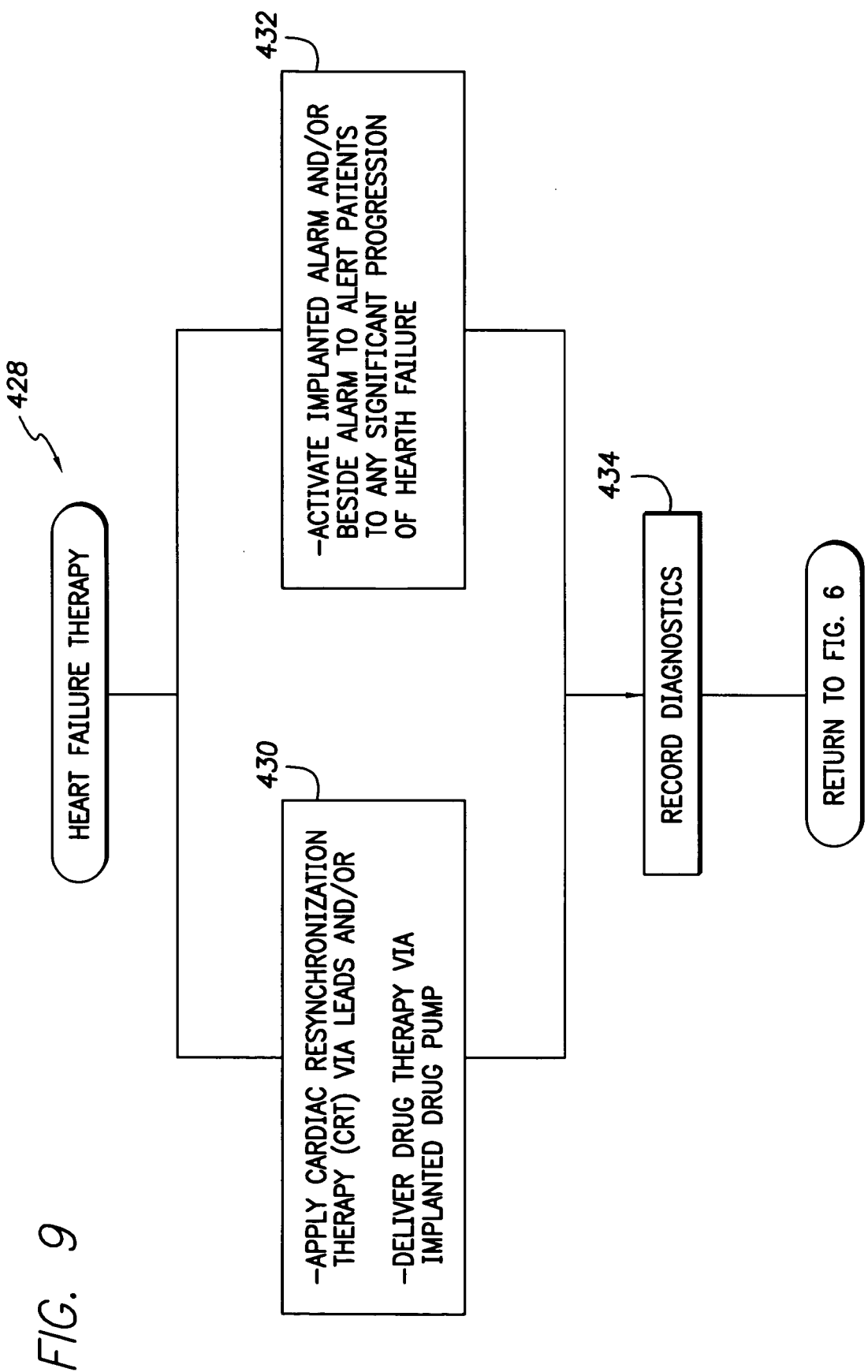
FIG. 9 is a flow chart illustrating exemplary techniques for delivering therapy in response to heart failure for use with the technique of FIG. 6.

Referring now to FIG. 9, heart failure therapy activated at step 428 of FIG. 6, will be summarized. At step 430, heart failure therapy controller 305 (FIG. 5) controls delivery of CRT and/or drug therapy to the patient. CRT and related therapies are discussed in the above-referenced patents to Mathis, et al., Kramer, et al., and Stahmann, et al. The degree of severity of heat failure may be used to control CRT pacing parameters such as the time delay between left and right ventricular pulses to provide, for example, more aggressive CRT for more severe heart failure. Drug therapy is delivered using an implanted drug pump, if one is provided. Exemplary heart failure medications include ACE inhibitors, diuretics, digitalis and compounds such as captopril, enalapril, lisinopril and quinapril. Depending upon the particular medication, alternative compounds may be required for use in connection with an implantable drug pump. Routine experimentation may be employed to identify medications for treatment of heart failure that are safe and effective for use in connection with an implantable drug pump. Dosages may be titrated based upon the severity of heart failure, taking into account any medications already delivered that may have already compensated for heart failure. Implantable drug pumps are discussed in U. S. Pat. No. 5,328,460 to Lord et al., entitled "Implantable Medication Infusion Pump Including Self-Contained Acoustic Fault Detection Apparatus", which is incorporated by reference herein.

Simultaneously, at step 432, the heart failure therapy controller may activate the implanted warning device or the bedside monitor, or both, to alert the patient to a significant progression in heart failure. The aforementioned patent to Lord et al. also discusses implantable "tickle" warning devices. As noted above, the bedside monitor may be directly networked with a centralized computing system for immediately notifying the physician of a significant increase in heart failure severity. At step 434, appropriate diagnostic information is stored within the memory 294 (FIG. 5) of the device for subsequent transmission to external programmer during a follow-up session with the patient for review by a physician, or for immediate transmission via the bedside monitor to the centralized computing system, is one is provided.

Once therapy has been activated, or on-going therapy has been adjusted, processing returns to step 402 of FIG. 6, where the 24-hour timer is reset to begin timing the next 24-hour period for generating the next histogram. Preferably, so as to conserve memory space, only two histograms are stored—the current histogram and one other histogram representative of previous data, such as the aforementioned running average histogram, or the like.

What have been described are exemplary systems and methods for evaluating heart failure. Those principles may be exploited using other implantable systems or in accordance with other techniques. Thus, while exemplary embodiments have been described, modifications can be made thereto without departing from the spirit and scope of the invention.

What is claimed is:

1. A method for evaluating heart failure within a patient using an implantable medical device, the method comprising:
   detecting values representative of patient heart rate and corresponding activity levels for the patient during a period of time when the patient is active;
   deriving cardiac fitness values by calculating individual ratios of rest-rate adjusted heart rates to corresponding activity levels detected during the period of time when the patient is active; and
   evaluating heart failure, if any, within the patient based on the cardiac fitness values.

2. The method of claim 1 wherein detecting values representative of heart rate and corresponding activity levels comprises determining whether the patient is active by comparing patient activity levels against an activity threshold representative of a minimum level of activity.

3. The method of claim 1 wherein detecting values representative of heart rate and corresponding activity levels comprises detecting activity levels using an implanted activity sensor.

4. The method of claim 1 wherein deriving cardiac fitness values is performed by calculating the ratio R for each of a pair of heart rate values and corresponding activity level values where:

$$R=(\text{Heart Rate}-\text{Rest Rate})/\text{Activity Level}.$$

5. The method of claim 1 wherein deriving a cardiac fitness value is performed by inputting a value representative of a maximum heart rate for the patient and then calculating the ratio R for each of a pair of heart rate values and corresponding activity level vales where:

$$R=(\text{Heart Rate}-\text{Rest Rate})/(\text{Heart Rate Reserve})/\text{Activity Level}$$

where Heart Rate Reserve is Maximum Heart Rate minus Rest Rate.

6. The method of claim 1 wherein evaluating heart failure, if any, within the patient is performed based on a plurality of cardiac fitness values derived from a plurality of detected heart rate values and corresponding active level values obtained during a plurality of periods of time while the patient is active.

7. The method of claim 6 wherein evaluating heart failure within the patient comprises:
   generating a histogram (H) based on the plurality of cardiac fitness values;
   deriving a numerical measure (M) of the histogram representative of a specified characteristic of the histogram; and
   evaluating heart failure based on the value of M.

8. The method of claim 7 wherein the numerical measure (M) of the histogram is representative of one or more of a centroid, mean, median or average of the histogram.

9. The method of claim 8 wherein evaluating heart failure within the patient comprises detecting the presence of heart failure by comparing M against a threshold indicative of heart failure.

10. The method of claim 8 wherein evaluating heart failure within the patient comprises determining the severity of heart failure by comparing M against a set of threshold values indicative of different levels of severity of heart failure.

11. The method of claim 7 wherein evaluating heart failure within the patient comprises tracking changes in the severity of heart failure by detecting differences between histograms generated from heart rate values and activity level values collected at different times.

12. The method of claim 11 wherein detecting differences between histograms generated from heart rate values and activity level values collected at different times comprises:
   deriving a numerical value (L) representative of a lag between at a plurality of histograms generated from heart rate values and activity level values collected over a plurality of days; and
   tracking changes in L over the plurality of days.

13. The method of claim 12 wherein a positive value of L is indicative of a regression in heart failure; whereas a negative value of L is indicative of a progression of heart failure.

14. The method of claim 1 wherein evaluating heart failure within the patient comprises detecting heart failure.

15. The method of claim 14 further comprising tracking changes in severity of heart failure to identify any significant progression in heart failure.

16. The method of claim 1 wherein evaluating heart failure, if any, within the patient comprises determining the severity of heart failure.

17. The method of claim 1 wherein evaluating heart failure within the patient comprises tracking changes in the severity of heart failure.

18. The method of claim 1 further comprising controlling delivery of therapy in response to the evaluation of heart failure.

19. The method of claim 18 wherein the implantable medical device is capable of biventricular cardiac pacing and wherein controlling delivery of therapy comprises:
   delivering cardiac resynchronization therapy (CRT) to the heart of the patient.

20. The method of claim 18 wherein an implantable drug pump is provided and wherein delivering therapy comprises delivering heart failure drug therapy to the patient using the drug pump.

21. The method of claim 1 wherein an implantable warning device is provided and further comprising generating warning signals based on the evaluation of heart failure.

22. The method of claim 1 wherein an external warning device is provided and further comprising transmitting appropriate signals to the external warning device based on the evaluation of heart failure.

23. The method of claim 1 further comprising controlling storage of diagnostic information indicative of the evaluation of heart failure.

24. A method for evaluating heart failure within a patient using an implantable medical device, the method comprising:
   detecting values representative of patient heart rate and corresponding activity levels for the patient during periods of time when the patient is active;
   deriving individual cardiac fitness values by calculating ratios of rest-rate adjusted heart rate values to corresponding activity level values for each of a plurality of pairs of heart rate values and corresponding activity level values detected during the periods of time while the patient is active, where rest rate is a predetermined rest heart rate of the patient;
   generating a histogram based on the individual cardiac fitness values; and
   evaluating the heart failure, if any, within the patient based on a numerical measure of the histogram.

25. A system for evaluating heart failure, the system comprising:
   a detection system operative to detect values representative of heart rate and corresponding activity levels for the patient during a period of time when the patient is active;
   a derivation unit operative to derive a cardiac fitness value based on individual ratios of rest-rate adjusted heart rates to corresponding activity levels detected during the period of time when the patient is; and
   a heart failure evaluation unit operative to evaluate heart failure, if any, within the patient based on the cardiac fitness values.

26. A system for detecting the progression of congestive heart failure (CHF) within a patient, the system comprising:
   means for detecting values representative of heart rate and corresponding activity levels for the patient during a period of time when the patient is active;
   means for deriving derive a cardiac fitness value based on individual ratios of rest-rate adjusted heart rates to corresponding activity levels detected during the period of time when the patient is active;
   means for evaluating heart failure, if any, within the patient based on the cardiac fitness values; and
   means for of controlling delivery of therapy in response to the evaluation of heart failure.

* * * * *